United States Patent
Breininger et al.

(10) Patent No.: US 11,335,017 B2
(45) Date of Patent: May 17, 2022

(54) REGISTRATION FACILITY, METHOD FOR REGISTERING, CORRESPONDING COMPUTER PROGRAM AND COMPUTER-READABLE STORAGE MEDIUM

(71) Applicant: Siemens Healthcare GmbH, Erlangen (DE)

(72) Inventors: Katharina Breininger, Erlangen (DE); Marcus Pfister, Bubenreuth (DE)

(73) Assignee: Siemens Healthcare GmbH, Erlangen (DE)

( * ) Notice: Subject to any disclaimer, the term of this patent is extended or adjusted under 35 U.S.C. 154(b) by 14 days.

(21) Appl. No.: 16/881,208

(22) Filed: May 22, 2020

(65) Prior Publication Data

US 2020/0380705 A1    Dec. 3, 2020

(30) Foreign Application Priority Data

May 28, 2019 (DE) .......................... 102019207803.6

(51) Int. Cl.
*G06T 15/00* (2011.01)
*G06T 7/33* (2017.01)
(Continued)

(52) U.S. Cl.
CPC .............. *G06T 7/344* (2017.01); *A61B 6/032* (2013.01); *A61B 6/463* (2013.01); *G06T 7/75* (2017.01);
(Continued)

(58) Field of Classification Search
CPC ... G06T 2219/2004; G06T 2207/30021; G06T 2207/10116; G06T 2207/30104;
(Continued)

(56) References Cited

U.S. PATENT DOCUMENTS 8,577,093 B2 * 11/2013 Friedman ........... G06K 9/00604
382/115
8,743,109 B2 * 6/2014 Blank ..................... G06T 15/08
345/419
(Continued)

FOREIGN PATENT DOCUMENTS

DE      102017203438 A1    9/2018

OTHER PUBLICATIONS

Wellens LM, Meulstee J, Van De Ven CP, Van Scheltinga CT, Littooij AS, Van Den Heuvel-Eibrink MM, Fiocco M, Rios AC, Maal T, Wijnen MH. Comparison of 3-dimensional and augmented reality kidney models with conventional imaging data in the preoperative assessment of children with Wilms tumors. JAMA network open. 201.*

(Continued)

*Primary Examiner* — Phu K Nguyen
(74) *Attorney, Agent, or Firm* — Lempia Summerfield Katz LLC

(57) ABSTRACT

A registration facility and a registration method are provided where a pre-interventionally generated simulation model of an examination object is registered with an intra-interventional live image. The simulation model is adapted to the live image using at least one simulated course line of an anatomical feature and/or an instrument by minimizing a line distance metric, specified as a cost function, for a distance between the simulated course line and an actual intra-interventional course of the instrument that is visible in the live image.

20 Claims, 3 Drawing Sheets

(51) Int. Cl.
  *G06T 19/20* (2011.01)
  *G06T 19/00* (2011.01)
  *G06T 7/73* (2017.01)
  *A61B 6/03* (2006.01)
  *A61B 6/00* (2006.01)

(52) U.S. Cl.
  CPC ............ *G06T 19/006* (2013.01); *G06T 19/20* (2013.01); *G06T 2207/10116* (2013.01); *G06T 2207/30241* (2013.01); *G06T 2210/41* (2013.01); *G06T 2219/2004* (2013.01); *G06T 2219/2021* (2013.01)

(58) Field of Classification Search
  CPC ....... G06T 2210/41; G06T 2207/30172; G06T 7/344; G06T 7/75; G06T 2207/30241; G06T 19/20; G06T 2219/2021; G06T 2207/10081; G06T 19/006; A61B 6/504; A61B 6/463; A61B 6/486; A61B 6/12; A61B 6/487; A61B 6/032; A61B 6/481; A61B 6/5235
  USPC ......................................................... 345/418
  See application file for complete search history.

(56) References Cited

U.S. PATENT DOCUMENTS

| | | | | |
|---|---|---|---|---|
| 9,761,054 | B2* | 9/2017 | Bronder | G06F 3/011 |
| 9,939,888 | B2* | 4/2018 | Wilson | G06F 3/011 |
| 10,332,315 | B2* | 6/2019 | Samec | A61B 5/746 |
| 10,732,708 | B1* | 8/2020 | Roche | G06F 3/011 |
| 10,893,844 | B1* | 1/2021 | Douglas | A61B 6/022 |
| 11,016,561 | B2* | 5/2021 | Selker | G06F 3/011 |
| 11,049,326 | B2* | 6/2021 | Samec | A61B 5/163 |
| 11,049,328 | B2* | 6/2021 | Powderly | G06F 3/04815 |
| 2010/0329529 | A1* | 12/2010 | Feldman | G06K 9/4619 382/131 |
| 2012/0200689 | A1* | 8/2012 | Friedman | G06K 9/00255 348/78 |
| 2018/0250076 | A1 | 9/2018 | Gemmel | |

OTHER PUBLICATIONS

Sadeghi AH, Bakhuis W, Van Schaagen F, Oei FB, Bekkers JA, Maat AP, Mahtab EA, Bogers AJ, Taverne YJ. Immersive 3D virtual reality imaging in planning minimally invasive and complex adult cardiac surgery. European Heart Journal-Digital Health. Nov. 2020;1(1):62-70.*

Breininger, K. et al., "Pre-operative operation simulation of endovascular interventions", Jun. 14, 2018. pp. 1-5.

Dubuisson, M-P., and Anil K. Jain. "A modified Hausdorff distance for object matching." Proceedings of 12th International conference on pattern recognition. vol. 1. IEEE, 1994. pp. 566-568.

German Office Action for German Application No. 10 2019 207 803.6 dated Apr. 1, 2020.

Mohammadi, Hossein, et al. "A numerical preoperative planning model to predict arterial deformations in endovascular aortic aneurysm repair." Annals of biomedical engineering 46.12 (2018): 2148-2161.

Roy, David, et al. "Finite element analysis of abdominal aortic aneurysms: geometrical and structural reconstruction with application of an anisotropic material model." The IMA Journal of Applied Mathematics 79.5 (2014): 1011-1026.

Toth, Daniel, et al. "Adaption of 3D models to 2D x-ray images during endovascular abdominal aneurysm repair." International Conference on Medical Image Computing and Computer-Assisted Intervention. Springer, Cham, 2015.

* cited by examiner

REGISTRATION FACILITY, METHOD FOR REGISTERING, CORRESPONDING COMPUTER PROGRAM AND COMPUTER-READABLE STORAGE MEDIUM

CROSS REFERENCE TO RELATED APPLICATIONS

This application claims the benefit of DE 102019207803.6 filed on May 28, 2019, which is hereby incorporated by reference in its entirety.

FIELD

Embodiments relate to a registration facility for the registration of a pre-interventional simulated model of an examination object to an intra-interventional live image of the examination object.

BACKGROUND

Advancing technical developments, for example in the fields of medicine, medical technology, computer technology and data processing are increasingly providing new possibilities for medical applications. For example, methods for registering two images of one patient obtained with different imaging modalities are known from the field of medical technology. The two images may be superimposed such that structures visible in both images are overlaid on one another. The calculation hardware available at present often provides this kind of registration to be performed intra-operatively, i.e. without unacceptable waiting times.

Simulation or modeling methods are known in which, for example, anatomical structures or the behavior thereof are simulated or modeled with a high degree of computing effort. This is done, for example, using finite element methods known from current research, although, at least with the calculation resources currently available, these cannot be executed in real time and therefore cannot be used intra-interventionally, i.e. during an intervention or procedure on a patient, in a meaningful and beneficial manner. For example, a calculation or updating cycle for such a simulation or a corresponding model may take several hours.

In principle it would be desirable, in order to support an attending physician, for example in the safe performance of an intervention consistent with advance planning, also to be able to provide information and data that are as comprehensive, detailed, and accurate as possible during the intervention. However, a possibly simple superimposition of a pre-interventional complex simulation or modeling with an intra-interventional live image, such has been used to date for simple images, is typically of little help only because, unlike the case in a pre-interventional situation in which a pre-interventional data set was recorded as the basis for the complex simulation or modeling, the anatomical situation usually changes during the respective intervention.

BRIEF DESCRIPTION AND SUMMARY

The scope of the present disclosure is defined solely by the appended claims and is not affected to any degree by the statements within this summary. The present embodiments may obviate one or more of the drawbacks or limitations in the related art.

Embodiments provide a useful and practicable intra-interventional use of complex pre-interventional simulations.

A registration facility is used, i.e. is configured, to register a pre-interventionally generated model of an examination object with or to at least one intra-interventional live image of the examination object. The model may be a 2D model, a 3D surface model, that is also known as a 2.5D model, or a 3D model. To acquire and process corresponding pre-interventional and intra-interventional data, the registration facility includes a processor and a data memory and a communication interface, that are connected to the processor. The pre-interventional data may, for example, be or include the model or data, for example a pre-interventional image data set, from which the model may be generated. The intra-interventional data may be or include at least the live image, i.e. an image or corresponding image data, showing the examination object in real time at the respective time during the intervention, or image data from which the live image may be generated or reconstructed.

The registration facility is configured to use the model, hereinafter called model for short, that shows a simulated intra-interventional state of the examination object and an instrument in the examination object provided to be used in the respective intervention that is visible in the live image on the basis of a pre-interventional image data set of the examination object, to determine a simulated course line or geometry of an anatomical feature of the examination object in the region of the instrument and/or a simulated course line or position of the instrument. It is provided that the planned intervention or the behavior of the examination object during the planned intervention is simulated on the basis of the pre-interventional image data set, that was recorded without any intervention and without the presence of the instrument in the examination object. Resulting geometric courses or arrangements of the examination object or at least one part of the examination object and the respective instrument used are then described by the simulated or calculated model. The pre-interventional image data set may be a 2D, 2.5D or 3D image data set or, as a 4D image data set, show a temporal development.

The examination object may, for example, be a patient, a subarea or organ of the patient, a vascular tree or a vessel or a part thereof or the like. Accordingly, the course line of the examination object may be, for example, a centerline of a vessel in or on which the instrument is to be guided or arranged during the intervention. The instrument may, for example, be a stent, a catheter, an endoscope, a probe, or the like. The course line of the instrument may, for example, correspond to a course, for example a longitudinal course, an outline, a centerline or the like of the instrument, i.e. show or describe a respective position and geometry of the instrument. It is advantageous to model and simulate both the course, i.e. the geometry, of the examination object and the course or the geometry of the instrument in combination with each other in the model since the instrument and the examination object come into mechanical contact with one another during the intervention and thus may exert a mutual influence on each other in respect of a position, a course, or a geometry.

Furthermore, the registration facility is configured to use the at least one live image to determine an actual intra-interventional course of the instrument. The actual course corresponds to the position and geometry of the instrument during the intervention at the time of the recording of the live image, i.e. shows a corresponding real and non-simulated arrangement of the instrument. The instrument may be X-ray opaque or at least include an X-ray opaque part of a medical device so that the instrument is visible without contrast medium in an X-ray image or fluoroscopic image recorded as the live image.

The registration facility is further configured to register the model automatically with or to the live image using at least one of the simulated course lines and the actual intra-interventional course of the instrument. The registration facility is configured to configure/adapt the model to the live image by minimizing a line distance metric, for example, a modified Hausdorff distance d, specified as a cost function or part of a cost function, between at least one of the simulated course lines X and the actual intra-interventional course Y of the instrument. The modified Hausdorff distance may be defined by or based on the equation:

$$d(X, Y)H = \max\left\{\frac{1}{|X|}\sum_{x \in X} \min_{y \in Y} \|x - y\|, \frac{1}{|Y|}\sum_{y \in Y} \min_{x \in X} \|x - y\|\right\}.$$

d(X,Y) designates a line distance between the lines X and Y, that are described by their coordinates or elements x or y, "max" designates the maximum, "min" designates the minimum and "$\| \|$" the norm of the respective variables.

To minimize the cost function defined by the modified Hausdorff distance d or based on the modified Hausdorff distance d, the model may, for example, be displaced, rotated, compressed, stretched or deformed in some other way, i.e. configured/adapted. The configuration does not entail a new simulation run of the model; i.e. the model is not completely recalculated or re-simulated to achieve the configuration. As described in the introduction, a calculation could take several hours and therefore is not practicable to perform during the intervention. Instead, embodiments use an alternative methodology by which the model is configured to the live image and may be registered therewith and that requires significantly less calculation effort and fewer calculation resources and is hence actually practicable to perform and apply in at least almost real time during the intervention.

The minimization of the line distance metric, for example, the named modified Hausdorff distance (MHD), the model, and the respective live image may be overlaid on one another in a simple, quick, and accurate manner which provides an accurate registration of the model to the live image to be achieved during the intervention, that provides the generation of a corresponding superimposed image from the model and the live image.

A superimposed image provides the respective attending physician or other staff members to be provided during the intervention with data and information that have not been available intra-interventionally. The present registration facility may support the performance of the intervention or corresponding staff members and contribute to a respective treatment outcome.

The registration facility is, for example, able to execute the described measures, processes or sequences automatically or semi-automatically, for example in that a corresponding specified computer program or operating program, that may, for example, be stored in the data memory, is executed by the processor.

The model may be a relatively complex model of the examination object as described in the introduction, for example a finite-element model and/or, for example, a hydrodynamically simulated flow model. The generation of the model may require certain assumptions to be made since a hundred percent realistic and accurate simulation of the behavior of the examination object and the instrument requires correspondingly exact knowledge of, for example, mechanical components of the examination object and the instrument and a movement of the instrument that actually takes place later during the intervention, that are never completely present at the time of the simulation. For this reason and due to the fact that, during the intervention, the examination object, for example the patient, is usually located in a position or location that has changed compared to the time of the recording of the pre-interventional image data set, to date there has a been a problem that the pre-interventional model does not reproduce the actual situation during the intervention sufficiently accurately to provide registration or superimposition with the live image to be performed with sufficient accuracy.

Embodiments provide a solution that does not subject the examination object to any additional stress since the reference point or reference element used for the registration is the course of the, for example radiopaque, instrument that is already visible in the live image and thus no additional administration of contrast medium is required for the registration. Embodiments provide robust, automatic, and contrast-medium-free registration of the pre-interventional or pre-operative model or the corresponding simulation to the live image, for example an intra-interventional fluoroscopic image. Embodiments provide the utilization or use of correspondingly complex pre-interventionally generated and calculated models or simulations during an intervention, i.e. as part of a clinical procedure.

The registration facility may be a stand-alone facility or stand-alone device, for example as a computer. The registration facility may also, for example, be part of a server or computer center or, for example, be integrated in a medical imaging device, for example an X-ray device, a computed tomography scanner, a magnetic resonance imaging system, an ultrasound device or the like. Accordingly, the facilities or elements of the registration facility, i.e. the processor, the data memory, and/or the communication interface, may then be shared, i.e. for example used by other facilities or for other functions.

The registration facility is able, for example, via the communication interface, to acquire the fully or completely simulated, i.e. calculated, model and store it in the data memory. The registration facility may also be configured to acquire the pre-interventional image data set or corresponding raw data from which the pre-interventional image data set may be constructed, for example via the communication interface, to reconstruct the actual image data set or to use the image data set to perform the calculation or simulation of the actual model to generate the final model of the examination object with the simulated course lines. The pre-interventional image data set may be a 3D CT image data set.

The determination of the course lines or centerlines may, for example, include a corresponding segmentation or image processing of the image data set, the model, or the live image that for example, may be implemented by the registration facility using methods that are known from medical image processing and data processing. The course lines or centerlines may also be determined by another facility and provided to the registration facility in the form of corresponding data. The "determination" of the course lines or centerlines or the actual course of the instrument may include the acquisition or reading out of corresponding data.

The modified Hausdorff distance may also be designated the Hausdorff distance or Hausdorff metric. MHD and/or the cost function may correspond to or contain the MHD may be based on the equation shown, for example, but may be or is also, for example, supplemented by a further factor, as a weighting factor or the like. It is also possible, for example in the case of the use of several course lines of the examination object and/or the use of several instruments or sections of instruments with respective individual actual courses, to determine several individual terms for the respective course lines, courses or corresponding pairs of lines or courses in the form shown above and then add them together in order to obtain a final overall MHD. However, it is also possible for other cost functions or line distances or line distance metrics to be specified and used in a corresponding manner.

The registration facility may be configured to generate an overlay, i.e. a superimposed image, from the configured model and the live image. The overlay or superimposed imposed may be registered to a respective imaging device, for example a C-arm or C-arm X-ray device, by which the live image was recorded which provides flexible and effective support to be offered during the intervention.

Embodiments may be used for endovascular procedures, such as EVAR (endovascular aneurysm/aorta repair), but also for cardiological or neurological interventions for example.

Neither the registration facility nor the other presently claimed aspects, for example the method described below, also claim an actual surgical step or intervention. On the contrary, the embodiments are directed at the operation of respective devices or facilities, for example the registration facility, or the processing of data provided. Therefore, any surgical steps or measures named or indicated to elucidate the embodiments may not be included. The registration facility may be used and operated in parallel with an intervention or a surgical procedure and the method may be carried out in parallel to an intervention or a surgical procedure. Embodiments may be used for the, for example automatic, support of the respective members of the medicinal staff and use data that may also be acquired and processed independently of the actual surgical steps performed. Embodiments may also be used logically and usefully on the basis of artificially generated data or subsequently on the basis of stored data for example. Even if the method may be performed at least partially during an intervention, ultimately, it may not relate to any surgical steps that may be performed but only to the operation or control of the registration facility and/or the processing of available data.

In an embodiment, the registration facility is configured to perform the registration as a 2D-3D registration by minimizing a 2D form or 2D formulation of the line distance metric, for example, the modified 2D Hausdorff distance, and to use a 2D projection image as the live image and to determine the at least one simulated course line, i.e. the simulated course line of the examination object and/or the instrument, from a 2D forward projection of the 3D model, i.e. also of the then three-dimensional model. The 2D forward projection may be generated by the actual registration facility from the 3D model. It is also possible for the 2D forward projection to be specified and provided to the registration facility, i.e. acquired thereby. The 2D forward projection generates a two-dimensional image from the three-dimensional model, that may be registered consistently with the two-dimensional live image. A superimposed image generated after or by the registration may also be a two-dimensional image.

A configuration of the two-dimensional image generated by the 2D forward projection performed for the registration may also be transferred to the complete 3D model since this contains all the structures contained in the two-dimensional image. For example, the configuration may be continued consistently into the third dimension or extrapolated in the dimension. A three-dimensional image containing both the 3D model and the 2D live image may be generated as a superimposed image.

The performance of the 2D-3D registration may be advantageous since, as described, due to the then identical dimensionality, the two-dimensional image generated from the 3D model by the 2D forward projection may be combined consistently with the 2D live image. In addition, the registration may then be performed quickly and with little effort since only a smaller data volume has to be handled and processed in the form of the projected two-dimensional image. A further advantage is that only one single 2D live image is required thus providing the registration to be performed at a time close to its recording time and quickly and with little stress for the examination object. The used modified 2D Hausdorff distance may, as described, be defined by the equation shown above or based thereon. The variables contained therein each have two coordinates or dimensions.

In an embodiment, the registration facility is configured to perform the registration as a 2×2D-3D registration or as a 3D-3D registration by minimizing a 3D form or 3D formulation of the line distance metric, for example, the modified 3D Hausdorff distance, and to determine the actual intra-interventional 3D course of the instrument from at least two 2D live images recorded from different angulations or estimate this using a 2D live image. The simulated course lines of the examination object or the instrument are also present as 3D course lines since the simulated course lines are determined using the 3D model, i.e. using the three-dimensional model.

The actual 3D course of the instrument may, for example, be determined by the registration facility itself or calculated by corresponding processing of the at least two different 2D live images. However, the actual 3D course of the instrument may also be determined or calculated by another facility, for example the medical device used to record the at least two different 2D live images and then provided to the registration facility, i.e. acquired thereby.

Reconstruction methods that are known may be used to determine the actual 3D course of the instrument from the at least two different 2D live images.

The performance of the registration as a 2×2D-3D or as a 3D-3D registration provides the respective staff members to be supported in an effective and flexible manner. Thus, the result may, for example, be the generation of a registered 3D superimposed image from the 3D model and the at least two different 2D live images or the actual 3D course of the instrument. The 3D superimposed image may be rotated by the respective staff members or, for example, observed from different directions or viewing angles without losing the correct spatial positional relationship between the configured 3D model and the real, i.e. actual, 3D course of the instrument. This allows the respective staff members to gain a good and accurate impression of a respective actual spatial situation during the intervention.

The actual intra-interventional course, i.e. a 3D position, of the instrument may also possibly be estimated from only one single 2D image or one single 2D view. The estimated 3D course may then be used for the 3D-3D registration.

In an embodiment, the registration facility is configured to deform the model r to configure the model to the live image. For example, a form, shape, or geometry of the simulated courses may be deformed such that the form, shape, or geometry corresponds to or follow the actual intra-interventional course of the instrument. Other components, points, or elements of the model may be treated as connected to the simulated course lines so that the components, points, or elements of the model may correspondingly follow suit or be included in the deformation of the simulated course lines. As a result, despite the deformation of the course lines, the model's consistency may be maintained. During the deformation of the model to configure to the live image, the model, and the live image may be overlaid accurately, and the registration and superimposition may therefore be performed precisely. For the deformation of the model, an as-rigid-as-possible assumption or specification (an English technical term) for the model may be taken into account and the elements or structures of the examination object simulated thereby. As a result, the configuration of the 2D image to the live image may be achieved by minimal and medicobiologically plausible deformations, thus providing the computing effort to be kept low and rendering the model more realistic.

In an embodiment, the registration facility is configured only to configure the model to the live image in a specified subset of all available or possible degrees of freedom. The registration facility may be configured only to perform translations or rotations. It is also, for example, possible for the configuration to be performed in only one or two specified directions or dimensions or in another subset of parameters which provides the complexity, and hence the computing effort, and the time and computing power required for the registration or configuration of the model to be reduced or kept low that in turn provides the registration to be performed in at least almost real time in order to be able to offer the respective staff members support during the intervention in the closest time possible.

The configuration of the specification of the subset of the degrees of freedom according to the situation may nevertheless achieve a meaningful result, i.e. for example a sufficiently accurate registration, for example if a treatment outcome requires congruence of the model and live image only in one certain direction or dimension or in one certain parameter. In order to achieve a high degree of accuracy in the direction or dimension or in the parameter, it is then possible—initially counterintuitively—to accept correspondingly greater deviations or inaccuracies with the superimposition or registration in other directions, dimensions, or parameters that provides a flexible and at the same time furthermore sufficiently accurate application in a wide variety of different situations, for example including when there are strict real-time requirements and/or, for example, only older or weaker calculation hardware is available.

In an embodiment the registration facility is configured when adapting the model to the live image only to take account of a specified subset of the instrument(s) visible in the live image, e.g. only to take account of certain parts, sub-regions or sections of the instrument(s) visible in the live image or only certain visible instruments or the corresponding actual courses, while other parts or sections of the instrument(s) or other complete instruments may be ignored. This may possibly reduce the calculation effort required for the configuration of the model or for the registration and hence the corresponding calculation time without necessarily impairing or endangering the respective treatment outcome.

For example, the decisive factor for the treatment outcome may be merely the position of a stent or a current position of a probe or needle or the like, while positions of other instruments, for example clamps, braces or the like arranged in a peripheral region are ultimately of no relevance. It is also, for example, possible for instruments to be used during the intervention that are not simulated in the model. The active exclusion of the consideration of such instruments and hence of corresponding, for example automatically recognized, courses or course lines provides the configuration of the model to be performed reliably and consistently. The subsets of the instrument(s) to be considered may, for example, be specified by the respective staff members, for example by manually marking the corresponding courses or corresponding segmented regions in the live image and/or in the model.

The registration facility may also be configured automatically to make an assignment between instruments simulated in the model and instruments visible in the live image and only to take account of instruments or courses of instruments that are both simulated in the model and visible in the live image.

A further embodiment provides where the registration facility automatically only takes account of such instruments or sections of instruments arranged within a specified region of interest (ROI), for example marked in the live image and/or in the model. This may minimize the calculation effort required. Since the region of interest will typically include a region of the examination object that is relevant for the respective treatment outcome, this will not impair the treatment outcome since any resulting inaccuracies during the configuration of the model or during the registration in regions that then lie outside the region of interest will typically have no significant influence on the registration or a corresponding depiction of a superimposed image in the region of interest.

In an embodiment, the registration facility is configured to modify, i.e. to weight, the cost function by at least one specified weighting factor in dependence on at least one specified parameter of the respective intervention. The parameter and the value thereof may, for example, already be specified when planning the intervention.

The parameter or a respective value of the specified parameter may also be automatically or semi-automatically recognized or determined using the available data, i.e. for example using the model and/or using the live image, for example by the actual registration facility. Using corresponding evaluation or processing of the data, the registration facility may, for example, automatically dynamically calculate or ascertain the parameter or the value of the specified parameter by a comparison of features or properties of the data with a specified assignment table, that may, for example, be stored in the data memory of the registration facility.

The registration facility may also be configured automatically to select the weighting factor to be used with respect to its nature or type and/or its value, for example also using a corresponding specified assignment table or the like, that is, for example, stored in the data memory of the registration facility.

The use of the weighting factor provides the application to be configured to different situations or interventions. For example, for different interventions or different instruments used or different anatomical regions, minimized distances in different regions or between different elements may in each case be more or less advantageous or decisive than others for a treatment outcome and the provision of effective support for the respective staff members during the intervention.

The parameter may for example be a type of instrument, an anatomical region in which the intervention is to be or will be performed, a pathological change to a vascular property of the examination object, a location and possibly an extent or degree of calcification or the like, etc.

For example, several course lines of the examination object, for example several centerlines of different vessels, and/or several actual intra-interventional and corresponding simulated courses of several instruments may be taken into account. However, a distance of a certain instrument, for example a stent, from a certain vessel, for example from a calcification in one of the vessels, may be of more importance for the treatment outcome than, for example, a distance of a further instrument, for example a supportive clamp or brace, from another point of the vessel or another vessel, and accordingly modified with a greater weighting factor.

Overall, this provides a flexible configuration to different situations and circumstances in a simple manner, thus providing the probability of a respective treatment outcome to be further improved.

In an embodiment, the registration facility is configured automatically to acquire updated live images as soon as the live images are available and automatically to configure the model to each newly acquired live image. The registration facility is configured to proceed from the most recently configured model, i.e. the most up-to-date model in each case. This provides an accurate and reliable registration and accordingly an accurate and reliable superimposed depiction to be achieved or ensured reliably and close to real time with a low calculation effort even in the case of changes to a situation or geometry during the intervention. The fact that the starting point used for each new configuration or update for each new or updated live image is the most recently configured model and not the original model provides necessary adaptations, for example displacements, rotations or deformations, of the respective model that has already been configured to a previous live image to be kept low.

Instead of performing the configuration for each new or updated live image, it is also possible for at least one criterion to be specified and evaluated on the acquisition of a new updated live image. The respective configuration is only performed when the criterion is fulfilled. Such a criterion may, for example, be that a difference between the current image in each case and a preceding live image for which the model was most recently configured is greater than a specified threshold value, for example with respect to a distance, i.e. a displacement of a point or a structure from one live image to the other, and/or with respect to a number of points or regions in which differences between the two respective live images may be detected. It is, for example, possible for each new live image to be compared with the previous live image in each case or with the live image to which the model was most recently configured. The criterion specified may, for example, be a time interval so that an configuration of the model is only performed when at least the specified time interval has elapsed in each case since the last configuration which may reduce the calculation effort and provide the system or method to be used with, for example, older or weaker calculation hardware.

In an embodiment, the registration facility is configured to perform a provisional registration of the model to the live image using solid non-deformable structures of the examination object that are visible in the pre-interventional image data set and/or in the model on the one hand and in the live image on the other before the registration of the model with the live image, for example before the determination of the simulated course lines and the actual intra-interventional course of the instrument. It is, for example, possible that structures or information that, although contained in the pre-interventional image data set, were not recorded in the model, cannot be used. The pre-interventional image data set may include of several data subsets, that might have possibly been recorded at different times. For example, the initial or provisional registration suggested may be performed on the basis of a first data subset, i.e. using images, that were, for example, recorded immediately before or at the start of the intervention, while the model may be generated using a second data subset, that, for example, was recorded several hours or days before the intervention.

Solid non-deformable structures may, for example, be or include a bone structure, a calcification or an artificially introduced marker or the like. The latter may then also be considered to be part of the examination object in the sense.

A provisional registration based on the solid non-deformable structures may be performed simply and quickly since the structures generally do not deform but are only displaced. However, such a provisional registration may be unable to reliably provide sufficient accuracy for soft parts or soft tissue in the environment of the solid non-deformable structures since it is quite possible for the solid non-deformable structures to undergo unpredictable deformation in the event of a displacement of structures. However, the provisional registration in the context is still advantageous since it provides the model to be aligned relative to the live image in a quick, simple, and reliable manner such that the subsequent registration and configuration of the model based on the minimization of the MHD typically only requires relatively fewer changes to the model than would be necessary without the provisional registration.

Since the solid non-deformable structures in the live image may be unequivocally and reliably detectable and identifiable, the procedure suggested may also improve the consistency or plausibility of the later configuration or registration of the model. For example, in the case of a greater change in the position and/or geometry of the examination object between the times at which the pre-interventional image data set and the live image are recorded it is possible to reduce the probability of incorrect assignment between regions or structures of the model and the live image. The provisional registration may, for example, be performed before or during the determination of the actual course of the instrument thus ultimately providing improved efficiency or speed to be achieved with the application.

Embodiments further provide a method, for example, a wholly or partially computer-implemented method, for registering a pre-interventionally generated model of an examination object with at least one intra-interventional live image of the examination object.

One method step of the method is or includes the generation or acquisition of the model that shows a simulated intra-interventional state of the examination object and an instrument in the examination object provided to be used in the intervention that is visible in the live image, i.e. an instrument that is visible in the examination object, with the imaging modality used therefor, on the basis of a pre-interventional image data set of the examination object.

A further step of the method is or includes using the model to determine a simulated course line of an anatomical feature of the examination object in the region of the instrument and/or a simulated course line of the instrument.

A further step of the method is or includes using the at least one live image to determine an actual intra-interventional course of the instrument.

A further step of the method is or includes the automatic registration of the model with the live image using at least one of the simulated course lines and the actual intra-interventional course of the instrument. The registration is performed with the configuration of the model to the live image by minimizing a line distance metric, for example a modified Hausdorff distance, specified as a cost function or as part of a cost function, between at least one of the simulated course lines and the actual intra-interventional course of the instrument. The modified Hausdorff distance may, but not necessarily, used as the line distance metric is also defined or based on the equation or relationship shown in connection with the registration facility. The method may be a method for operating or controlling the registration facility or an imaging device or system including the registration facility. Accordingly, further processes, courses or measures mentioned in connection with the method and/or the other aspects may constitute further optional method steps of the method.

A further aspect is a computer program including or implementing commands or control instructions, that, on the execution of the computer program by a computer, for example by the registration facility or the processor thereof, prompt the computer at least to execute the method steps of the method automatically or semi-automatically or prompt the execution of the method steps by the corresponding actuation of corresponding devices or facilities.

A further aspect is a computer-readable storage medium on which at least one embodiment or configuration of the computer program or computer program product is stored. The registration facility may include such a computer-readable storage medium, for example, as the data memory mentioned in connection with the registration facility or as part thereof.

A further aspect is a data carrier signal that transmits the computer program.

The properties and developments of the registration facility, the method, the computer program and the computer-readable storage medium and the corresponding advantages disclosed above and below may in each case be transferred analogously between the aspects.

DETAILED DESCRIPTION

Figure 1:
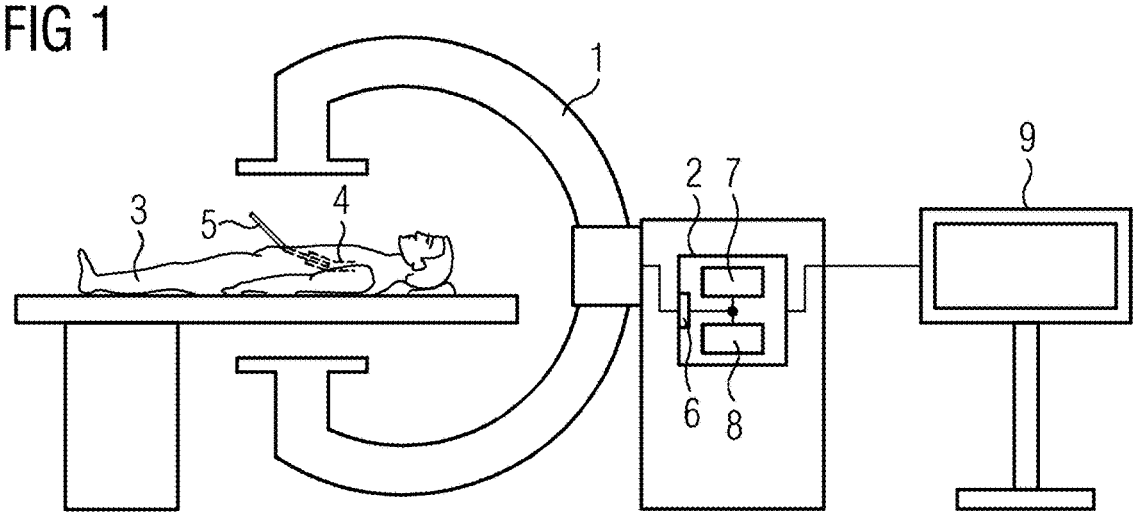
FIG. 1 depicts a schematic overview of a system including an X-ray device and an integrated registration facility according to an embodiment.

FIG. 1 is a schematic overview of an imaging system including an X-ray device 1 and a registration facility 2 integrated therein. The imaging system may be used to examine or map a patient 3, for example a vascular structure of the patient 3, designated a vessel 4. The vascular structure may, for example, include one single vessel, two or more vessels or vascular segments, a bifurcation region, or at least a part of a vascular tree. The X-ray device 1 is configured as a C-arm X-ray device with a C-shaped arm on the ends of which an X-ray source and an X-ray detector opposite thereto are held. An intervention is to be performed on the patient 3 in the course of which an instrument 5 is to be introduced into the vessel 4 or positioned in the vessel 4.

The registration facility 2 is provided as part of a data processing facility of the imaging system and includes a communication interface 6 to receive or acquire data, for example from image data acquired by the X-ray device 1 and from user inputs. The registration facility 2 further includes a processor 7 and a data memory 8, that are connected to the communication interface 6. A screen 9 on which, for example, images generated by the X-ray device 1 and/or by the registration facility 2 may be displayed is provided as part of the imaging system.

With reference to FIG. 1, the following is intended to describe a method that provides pre-operative or pre-interventional simulations, for example endovascular procedures, for example simulations of or for aortic aneurysm repair (EVAR) to be registered and used and automatically intra-operatively or intra-interventionally. Corresponding pre-operative EVAR simulations and other corresponding simulations for medical interventions currently still represent a relatively new field of research. The object is, in order to plan an intervention, to provide the prediction of behavior that actually occurs intra-operatively and possibly probable complications before the intervention using pre-operative data. With the example of an EVAR, this may, for example, mean that a CT image data set recorded pre-operatively may be used to answer or predict how the vessel 4 will be deformed, where and that shear forces will act on the vessel 4 and the instrument 5 introduced therein, how, for example in the case of relatively highly curved aortas, an introduced stent will expand and configure itself to the vessel 4, whether and how endo-leaks or stent displacements may be prevented and how blood flow through the introduced stent will possibly change.

A planning, and later attending, physician, and a manufacturer of the stent or the device, may use a simulation or the corresponding prediction as the basis for predicting at least potentially undesirable situations or complications and avoiding them, for example, by correspondingly changed planning and performance of the intervention or a correspondingly changed embodiment of the stent or other devices. The simulations required for this may usually only be performed pre-operatively by relatively time-consuming calculations, for example taking several hours, for example based on finite elements and/or flow simulations. However, it would in principle be desirable to use the corresponding simulations or models during the later intervention, for example in the form of an overlay registered to the X-ray device 1

The simulations are typically only the subject of research and possibly instrument development; however, endovascular interventions, for example, are not usually simulated pre-operatively in routine clinical practice.

Embodiments provide a method with which a pre-operative simulation may be configured automatically, flexibly, quickly and without the additional administration of contrast medium to actual intra-operative circumstances thus providing the best possible conformity between the simulation and an actual intra-interventional location or situation of the respective examination object to be achieved. Automatic and contrast-medium-free registration may provide the pre-operative simulation to be used as an overlay during the intervention.

Figure 2:
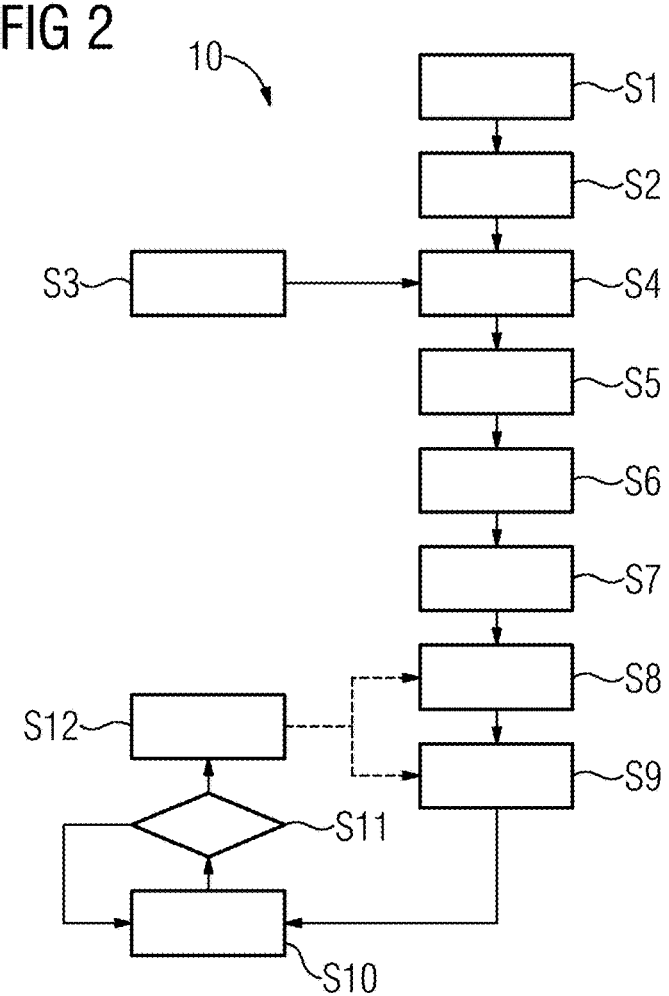
FIG. 2 depicts a schematic flowchart for a method for registering a simulated model of an examination object with a live image according to an embodiment.

FIG. 2 depicts a schematic flowchart 10 for a corresponding method. In a method step S1 a pre-interventional image data set, in the present case a 3D image data set of the respective examination object, is recorded, i.e. in the present case of the patient 3 or the vessel 4, for example as a 3D CT image data set by the X-ray device 1. A pre-interventional 3D image of the examination object is reconstructed from the 3D image data set.

In a method step S2, the reconstructed 3D image of the examination object is segmented and a three-dimensional initial or starting model of the examination object is generated as the basis for a later simulation.

In a method step S3, the registration facility acquires the parameters for the planned intervention or procedure, for example in the form of corresponding user inputs. The corresponding user inputs may, for example, indicate where, how, with which instruments and in accordance with which procedure, for example along which instrument path, etc., the intervention is to be performed. Unless the reconstruction of the 3D image or the segmentation or generation of the starting model of the examination object has already been performed by the registration facility 2, the segmentation or segmented starting model of the examination object by the registration facility is also acquired or read-in here.

In a method step S4, initially parameters for the simulation of the planned intervention are established or selected using the acquired parameters. It is possible for a level of detail, a simulated run time, a target region or region of interest and/or the like to be established for the planned simulations automatically or semi-automatically by the registration facility 2 or manually by corresponding operators. Then, the corresponding simulation is performed on the basis of the starting model, i.e. the planned intervention is simulated or modelled that results in a three-dimensional model, designated a 3D model 11 (see FIG. 3, 4) of the examination object showing a simulated intra-interventional state of the examination object and an instrument in the examination object used herein in or on the examination object. The simulated 3D model 11 contains simulated course lines or geometries of the vessel 4 and the instrument 5. The course lines are determined in a method step S5, i.e. for example extracted or read out from the 3D model 11.

Figure 3:
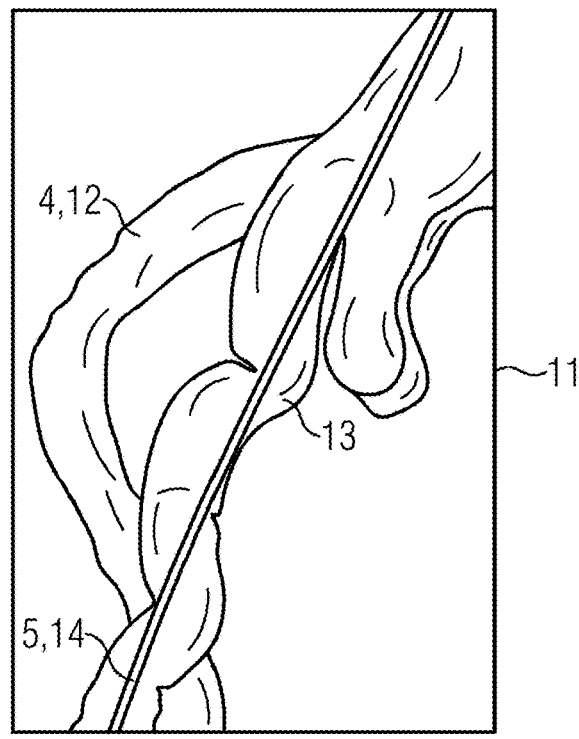
FIG. 3 depicts a schematic sectional view of the model with an original vascular course and simulated intra-interventional courses of the vessel and an instrument according to an embodiment.

FIG. 3 depicts a schematic sectional view of the 3D model 11 with an initial course 12 corresponding to an original vascular course of the vessel 4 before the start of the simulated intervention and at the recording time of the pre-interventional 3D image data set and with a simulated intra-interventional course 13 of the vessel 4 and with a simulated intra-interventional position 14 of the instrument 5. The introduction of the more rigid instrument 5 has caused the vessel 4 to be configured thereto, i.e. to be deformed.

The above-described method steps S1 to S5 are carried out before the actual intervention. During the later actual intervention, at least one live image of the examination object, that maps the instrument 5 in its actual intra-interventional course 16 (see FIG. 4, 5) in the vessel 4, is then recorded in a method step S6. The instrument 5 may be configured as X-ray opaque so that it is accordingly visible in the recorded live image independently of any contrast medium administration.

In a method step S7, a provisional registration of the 3D model 11 with the recorded live image is performed based on bone structures of the examination object, i.e. the patient 3, to achieve a reliable coarse alignment of the 3D model 11 to the live image.

In a method step S8, a fine registration of the 3D model 11 to or with the live image is then performed using the simulated course 13 of the vessel 4 and/or using the simulated position 14 of the instrument 5 and the actual intra-interventional course 16 of the instrument 5 extracted or segmented from the live image, i.e. detected in the live image. To achieve an improvement compared to the provisional registration based on the bone structures, the 3D model 11 is configured to the live image by minimizing a specified cost function. In the present case, a modified Hausdorff distance between the simulated course 13 and/or the simulated position 14 on the one hand and the actual intra-interventional course 16 of the instrument 5 is used as the cost function or the basis for the cost function. The cost function or the Hausdorff distance may, for example, be configured by one or more weighting factors in dependence on individual details or parameters of the respective intervention. The configuration of the 3D model 11 to the live image to minimize the Hausdorff distance or the cost function may, for example, displace, rotate, and/or deform the 3D model 11.

In a method step S9, a superimposed image 17 (see FIG. 4) is generated, for example also by the registration facility 2, from the correspondingly configured 3D model 11 and the live image, that are now registered with one another. In the superimposed image 17, it is possible for further data to be considered or elements to be inserted or image improvements to be added, for example to improve the contrast or distinguishability of different tissue regions or the like. The superimposed image 17 generated is then output, i.e. displayed, by the screen 9.

In a method step S10, a new, i.e. updated, live image of the examination object is recorded in the course of the intervention.

In a method step S11, the registration facility 2 automatically checks a specified criterion for an updating of the configured model. If the criterion is not met, the next updated live image in each case is awaited and then the criterion checked again. However, if the criterion is met, the more recently generated configured 3D model 11 in each case or the corresponding registration with the respective live image is configured to the most recently recorded, i.e. newest or most up-to-date, live image based on the most recently or previously configured 3D model 11 in each case. This is indicated here by corresponding dashed program paths to method steps S8 or S9.

The schematically represented method steps S1 to S12 of the flowchart 10 in FIG. 2 may represent corresponding facilities, circuits, software modules or functions of the registration facility 2 that execute the described method steps S1 to S12 or prompt their execution. Thus, a computer program corresponding to the flowchart 10 may, for example, be stored in the data memory 8 and executed by the processor 7.

Figure 4:
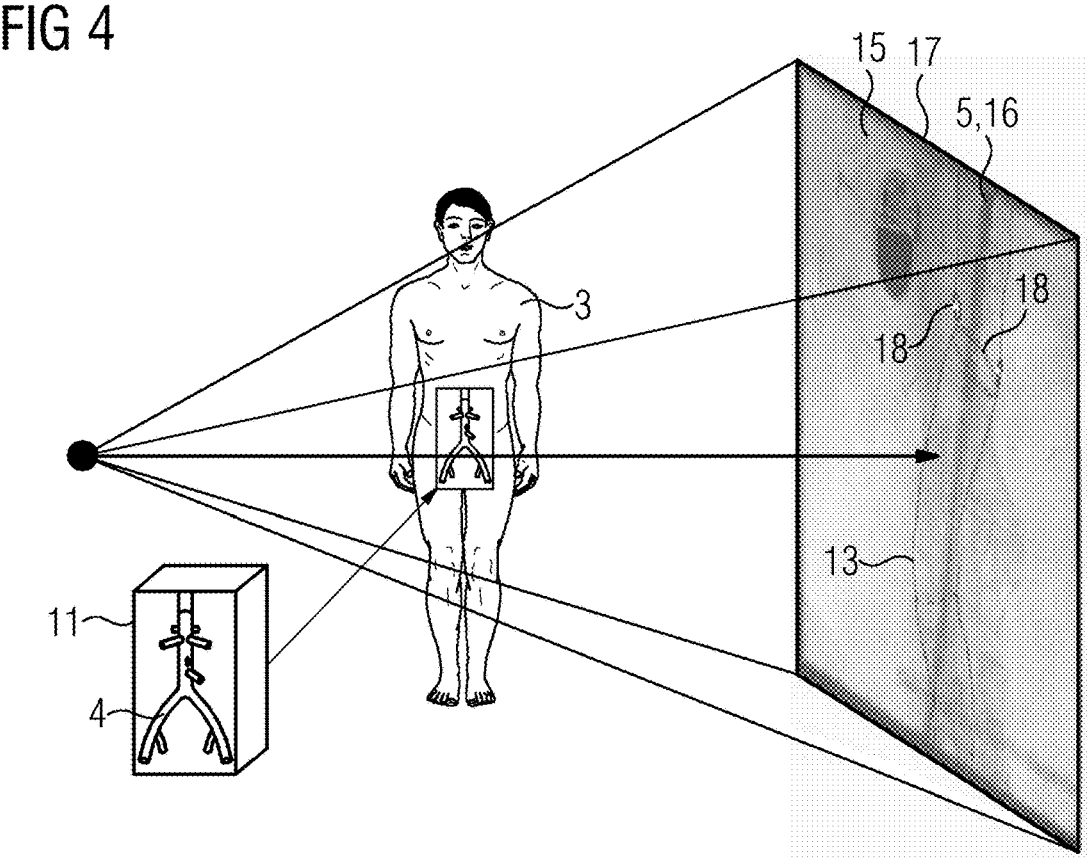
FIG. 4 depicts a schematic overview to illustrate the fusion of the simulated model with the live image according to an embodiment.

FIG. 4 is a schematic overview to illustrate a combination or fusion of the 3D model 11 with the live image, in the form of a fluoroscopic image 15. The fluoroscopic image 15 is a 2D image of a part of the patient 3. The actual course 16 of the instrument 5 is visible in the fluoroscopic image 15. Since the instrument 5 is guided within the vessel 4 during the intervention considered, the vessel 4 automatically follows the actual course 16 of the instrument 5 during the intervention. Therefore, if the simulated course 13 of the vessel 4 or the simulated position 14 of the instrument 5 in the 3D model 11 deviates here from, i.e. for example intersects the actual course 16, a corresponding configuration of the 3D model 11 is necessary to reflect the actual situation represented by the fluoroscopic image 15 during the intervention.

To provide a consistent combination here, a two-dimensional projection image of an examination region mapped by the fluoroscopic image 15 is also generated from the 3D model 11 by a 2D forward projection that is indicated schematically. The fluoroscopic image 15 and the two-dimensional projection image generated from the 3D model 11 are then superimposed on one another by the or after the described registration and configuration in order to generate the superimposed image 17. In addition, to generate or during the generation of the superimposed image 17, to further support the staff members, some virtual elements 18 are inserted in order to, for example, illustrate spatial or geometric relationships and/or to mark distinctive points or structures.

Figure 5:
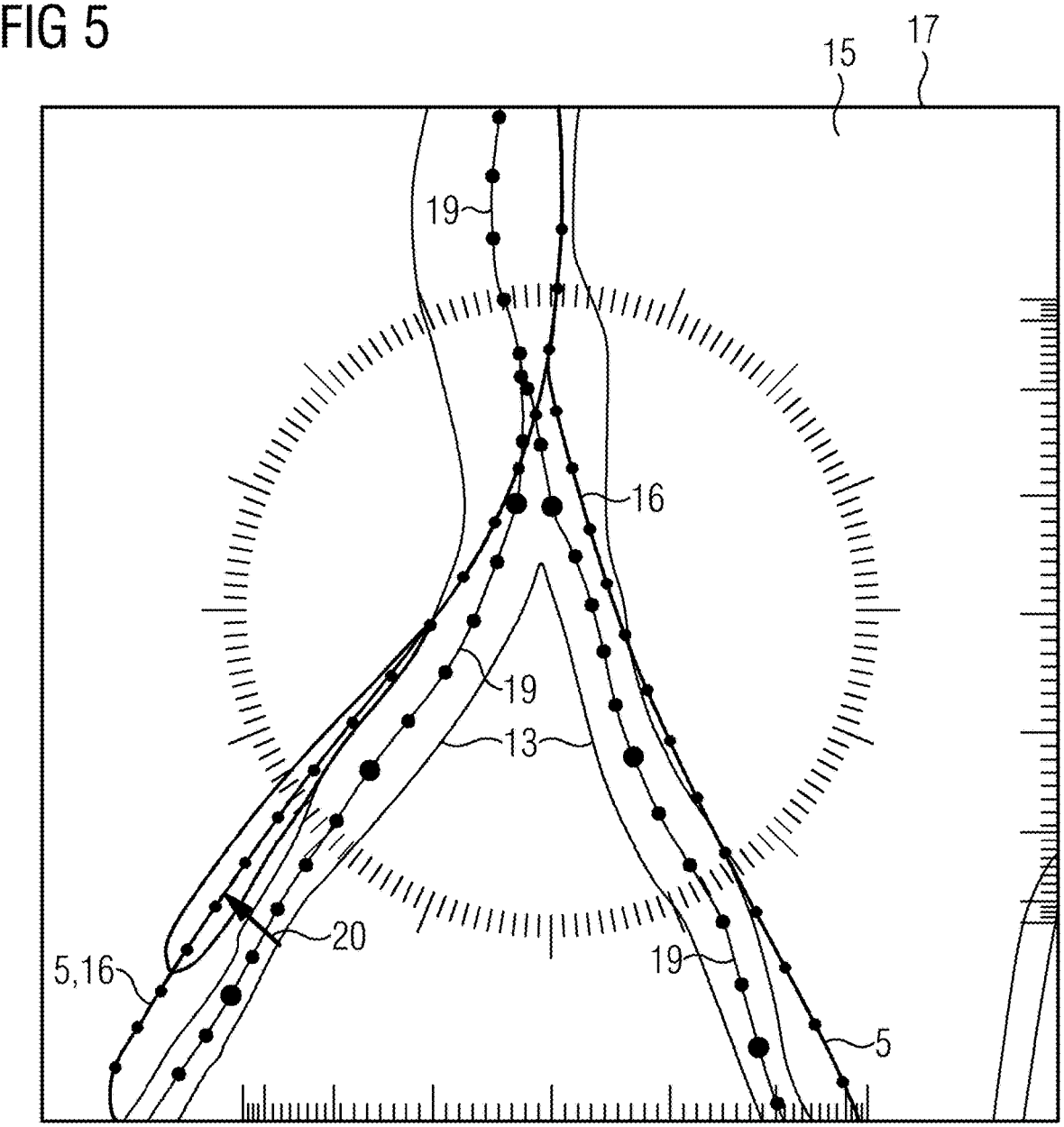
FIG. 5 depicts a schematic view of a superimposed image generated from the model and the live image according to an embodiment.

FIG. 5 is a further schematic view of the or a superimposed image 17 that depicts a or the fluoroscopic image 15 with the actual intra-interventional course 16 of the instrument 5. This is superimposed with the simulated course 13 of the vessel 4 and the centerline 19 thereof. The instrument 5 or the actual course 16 thereof lies partially outside the simulated course 13 of the vessel 4, that is evidently inconsistent or incorrect and accordingly has to be corrected by adapting the 3D model 11. An configuration is indicated schematically by an arrow 20 showing a direction in which the simulated course 13 of the vessel 4 or the corresponding centerline 19 has to be displaced to achieve an overlay with the actual course 16 of the instrument 5 that must be located within the real vessel 4.

Although, here, the superimposition or registration is shown schematically and by way of example for two dimensions, the method may be used analogously in three dimensions. In the case of a 2D-3D registration, a projected line of the respective vascular course and/or a simulated course or the simulated position 14 of the instrument 5 onto a corresponding 2D line, i.e. onto the actual course 16 of the instrument 5 recognized in the respective live image, is registered. In the case of 2×2D-3D or 3D-3D registration, a simulated 3D line of the simulated course 13 or the simulated position 14 of the instrument 5 onto a reconstructed 3D line, i.e. the three-dimensional actual course 16 of the instrument 5 recognized in the corresponding fluoroscopic images 15 and correspondingly reconstructed, is registered.

Overall, the described examples show how it is possible to provide a useful and practicable intra-interventional use of even complex pre-interventional simulations.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A registration facility for registering a pre-interventionally generated model of an examination object with at least one intra-interventional live image of the examination object, the registration facility comprising a processor and a data memory connected thereto and a communication interface, the registration facility configured to:
generate the pre-interventionally generated model comprising a simulated intra-interventional state of the examination object and an instrument in the examination object provided to be used in a respective intervention on a basis of a pre-interventional image data set of the examination object;
determine, with the pre-interventionally generated model, at least one of a simulated course line of an anatomical feature of the examination object in a region of the instrument or a simulated course line of the instrument;
determine, with the at least one intra-interventional live image, an actual intra-interventional course of the instrument;
register the pre-interventionally generated model with the at least one intra-interventional live image using at least one of the simulated course lines and the actual intra-interventional course of the instrument; and
adapt the pre-interventionally generated model to the at least one intra-interventional live image by minimizing a line distance metric of a cost function for a distance between at least one of the simulated course lines and the actual intra-interventional course of the instrument.

2. The registration facility of claim 1, wherein the line distance metric comprises a modified Hausdorff distance d that is defined by:

$$d(X, Y)H = \max\left\{\frac{1}{|X|}\sum_{x \in X} \min_{y \in Y} \|x - y\|, \frac{1}{|Y|}\sum_{y \in Y} \min_{x \in X} \|x - y\|\right\}.$$

3. The registration facility of claim 1, wherein the registration facility is further configured to perform the registration as a 2D-3D registration by minimizing a 2D line distance metric and to use a 2D projection image as the at least one intra-interventional live image and to determine the at least one simulated course line from a 2D forward projection of the pre-interventionally generated model configured as a 3D model.

4. The registration facility of claim 1, wherein the registration facility is further configured to perform the registration as a 2×2D-3D registration or as a 3D-3D registration by minimizing a 3D line distance metric and to determine the actual intra-interventional 3D course of the instrument from at least two 2D live images recorded from different angulations or estimated from a single 2D live image.

5. The registration facility of claim 1, wherein the registration facility is configured to adapt the pre-interventionally generated model by deforming the pre-interventionally generated model to the at least one intra-interventional live image.

6. The registration facility of claim 1, wherein the registration facility is configured to adapt the pre-interventionally generated model to the at least one intra-interventional live image only in a specified subset of all available degrees of freedom.

7. The registration facility of claim 1, wherein the registration facility is configured to take account of only a specified subset of instruments visible in the at least one intra-interventional live image when adapting the pre-interventionally generated model to the at least one intra-interventional live image.

8. The registration facility of claim 1, wherein the registration facility is configured to adapt the pre-interventionally generated model using a modified cost function that includes at least one specified weighting factor in dependence on at least one specified parameter of the respective intervention.

9. The registration facility of claim 8, wherein the at least one specified parameter is at least one of a type of instrument, an anatomical region in which the respective intervention is to be performed, or a pathological change in a vascular property of the examination object.

10. The registration facility of claim 1, wherein the registration facility is further configured to automatically acquire updated live images as soon they are available and automatically to adapt the pre-interventionally generated model to each newly acquired live image.

11. The registration facility of claim 1, wherein the registration facility is further configured to perform a provisional registration of the pre-interventionally generated model to the at least one intra-interventional live image using solid non-deformable structures of the examination object that are visible both in the pre-interventional image data set and also in the at least one intra-interventional live image using a bone structure, calcification and/or a marker before the registration of the pre-interventionally generated model with the at least one intra-interventional live image, before the determination of simulated course lines and the actual intra-interventional course of the instrument.

12. A method for registering a pre-interventionally generated model of an examination object with at least one intra-interventional live image of the examination object, the method comprising:
acquiring the pre-interventionally generated model, the pre-interventionally generated model depicting at least a simulated intra-interventional state of the examination object and the examination object provided to be used in a respective intervention that is visible in the at least one intra-interventional live image on a basis of a pre-interventional image data set of the examination object;
determining, using the pre-interventionally generated model, a simulated course line of at least one anatomical feature of the examination object in a region of an instrument, a simulated course line of the instrument, or the simulated course line of at least one anatomical feature of the examination object in the region of the instrument and the simulated course line of the instrument;
determining an actual intra-interventional course of the instrument using the one intra-interventional live image;
registering the pre-interventionally generated model with the at least one intra-interventional live image using at least one of the simulated course lines and the actual intra-interventional course of the instrument;
adapting the pre-interventionally generated model to the at least one intra-interventional live image by minimizing a cost function comprising a line distance metric for a distance between at least one of the simulated course lines and the actual intra-interventional course of the instrument.

13. The method of claim 12, wherein the line distance metric comprises a modified Hausdorff distance d that is defined by:

$$d(X, Y)H = \max\left\{\frac{1}{|X|}\sum_{x \in X} \min_{y \in Y} \|x - y\|, \frac{1}{|Y|}\sum_{y \in Y} \min_{x \in X} \|x - y\|\right\}.$$

14. The method of claim 12, wherein registering comprises a 2D-3D registration by minimizing a 2D line distance metric and to use a 2D projection image as the at least one intra-interventional live image and to determine the at least one simulated course line from a 2D forward projection of the pre-interventionally generated model configured as a 3D model.

15. The method of claim 12, wherein registering comprises a 2×2D-3D registration or as a 3D-3D registration by minimizing a 3D line distance metric and to determine the actual intra-interventional 3D course of the instrument from at least two 2D live images recorded from different angulations or estimated from a single 2D live image.

16. The method of claim 12, wherein adapting comprises deforming the pre-interventionally generated model to the at least one intra-interventional live image.

17. The method of claim 12, wherein adapting comprises adapting using a specified subset of all available degrees of freedom.

18. The method of claim 12, wherein adapting comprises taking account of only a specified subset of instruments visible in the at least one intra-interventional live image.

19. A non-transitory computer implemented storage medium that stores machine-readable instructions executable by at least one processor for registering a pre-interventionally generated model of an examination object with at least one intra-interventional live image of the examination object, the machine-readable instructions comprising:
acquiring the pre-interventionally generated model, the pre-interventionally generated model depicting at least a simulated intra-interventional state of the examination object and the examination object provided to be used in a respective intervention that is visible in the at least one intra-interventional live image on a basis of a pre-interventional image data set of the examination object;
determining, using the pre-interventionally generated model, a simulated course line of at least one anatomical feature of the examination object in a region of an instrument, a simulated course line of the instrument, or the simulated course line of at least one anatomical feature of the examination object in the region of the instrument and the simulated course line of the instrument;
determining an actual intra-interventional course of the instrument using the at least one intra-interventional live image;
registering the pre-interventionally generated model with the at least one intra-interventional live image using at least one of the simulated course lines and the actual intra-interventional course of the instrument; and
adapting the pre-interventionally generated model to the at least one intra-interventional live image by minimizing a cost function comprising a line distance metric for a distance between at least one of the simulated course lines and the actual intra-interventional course of the instrument.

20. The non-transitory computer implemented storage medium of claim 19, wherein the line distance metric comprises a modified Hausdorff distance d that is defined by:

$$d(X, Y)H = \max\left\{\frac{1}{|X|}\sum_{x \in X} \min_{y \in Y}\|x - y\|, \frac{1}{|Y|}\sum_{y \in Y} \min_{x \in X}\|x - y\|\right\}.$$

\* \* \* \* \*